United States Patent [19]

O'Boyle

[11] Patent Number: 5,019,055

[45] Date of Patent: May 28, 1991

[54] FLOW REGULATOR AND METHOD

[76] Inventor: Matthew O'Boyle, 310 Hall Hill Rd., Sommers, Conn. 06071

[21] Appl. No.: 454,983

[22] Filed: Dec. 22, 1989

[51] Int. Cl.$^5$ .............................................. A61M 5/00
[52] U.S. Cl. ................................. 604/249; 604/251; 251/342
[58] Field of Search ................ 604/33, 246, 249, 251, 604/252, 254, 255; 138/46; 251/342

[56] References Cited

U.S. PATENT DOCUMENTS

| | | | |
|---|---|---|---|
| 2,090,273 | 8/1937 | Wagner | 604/254 |
| 2,518,165 | 8/1950 | Millard | 138/46 |
| 3,227,173 | 1/1966 | Bernstein | 604/254 |
| 3,348,543 | 10/1967 | Stafford | 604/249 |
| 3,517,909 | 6/1970 | Santomieri | 251/342 |
| 3,547,401 | 12/1970 | Beall | 251/342 |
| 3,667,464 | 6/1972 | Alligood, Jr. | 604/254 |
| 3,877,428 | 4/1975 | Seagle et al. | |
| 4,103,686 | 8/1978 | LeFevre | 604/249 |
| 4,175,558 | 11/1979 | Hess, III et al. | |
| 4,640,306 | 2/1987 | Fan | 251/342 |
| 4,931,050 | 6/1990 | Idriss | 604/246 |
| 4,947,154 | 8/1990 | Hwang | 604/254 |

Primary Examiner—Stephen C. Pellegrino
Assistant Examiner—Ralph A. Lewis
Attorney, Agent, or Firm—Antonelli, Terry, Stout & Kraus

[57] ABSTRACT

A flow regulator for liquid to be administered parenterally to a patient comprises a first member having a flow passage therein for the liquid and a second member arranged to be adjustably telescoped in the passage. The first and second members are constructed such that they can be telescopingly positioned to form a flow rate controlling channel which restricts the flow rate as a function of the length of the channel. The length of the channel is adjustable by changing the relative position of the first and second members. An adjustment force applied to the outside of the regulator is transmitted to the second member within the flow regulator for changing the channel length and therefore the flow rate. The flow regulator can include a drip chamber positioned immediately above the second member for convenient adjustment of the flow rate. Sealing against leakage of air into the flow regulator is attainable because the flow rate controlling second member is located entirely within the first member.

24 Claims, 5 Drawing Sheets

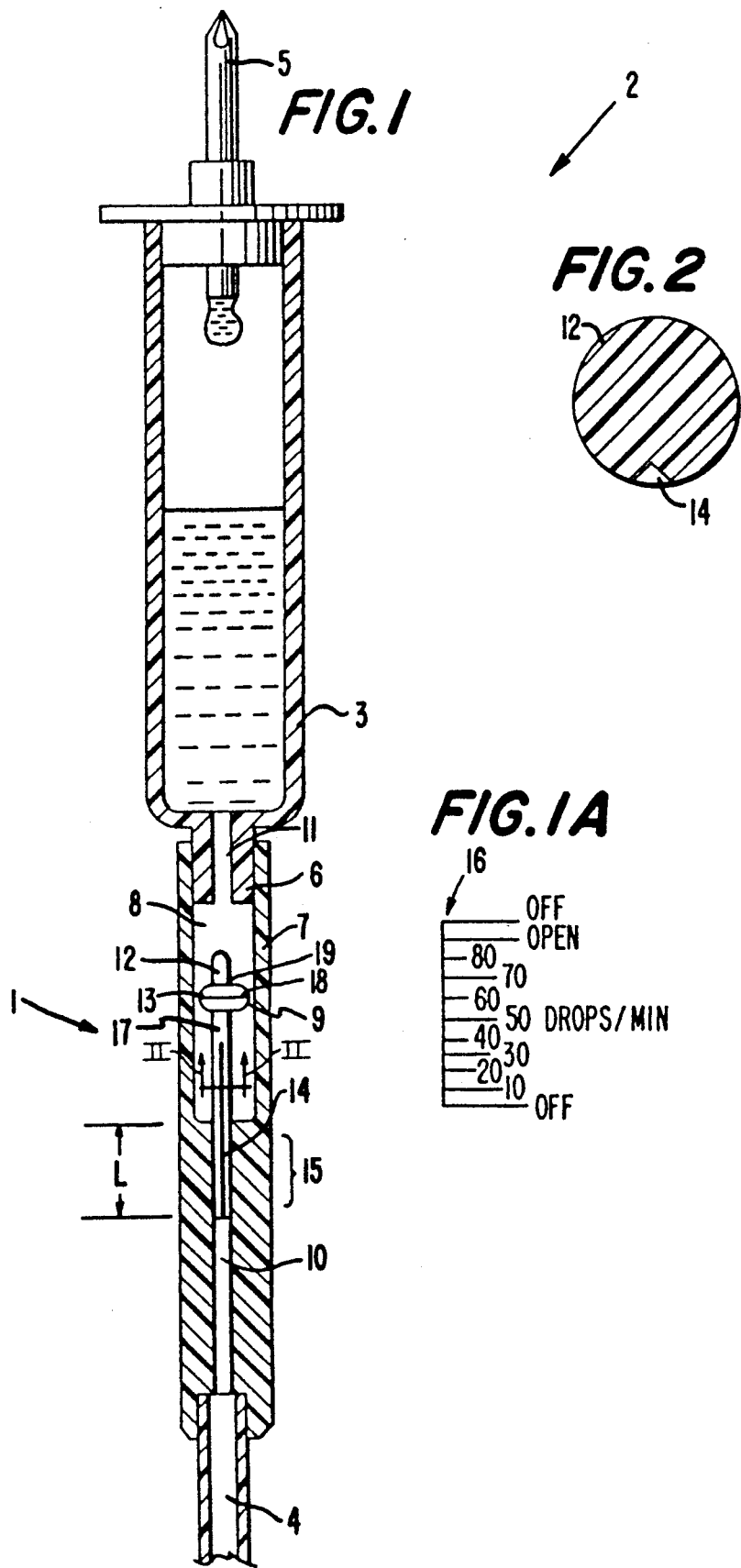

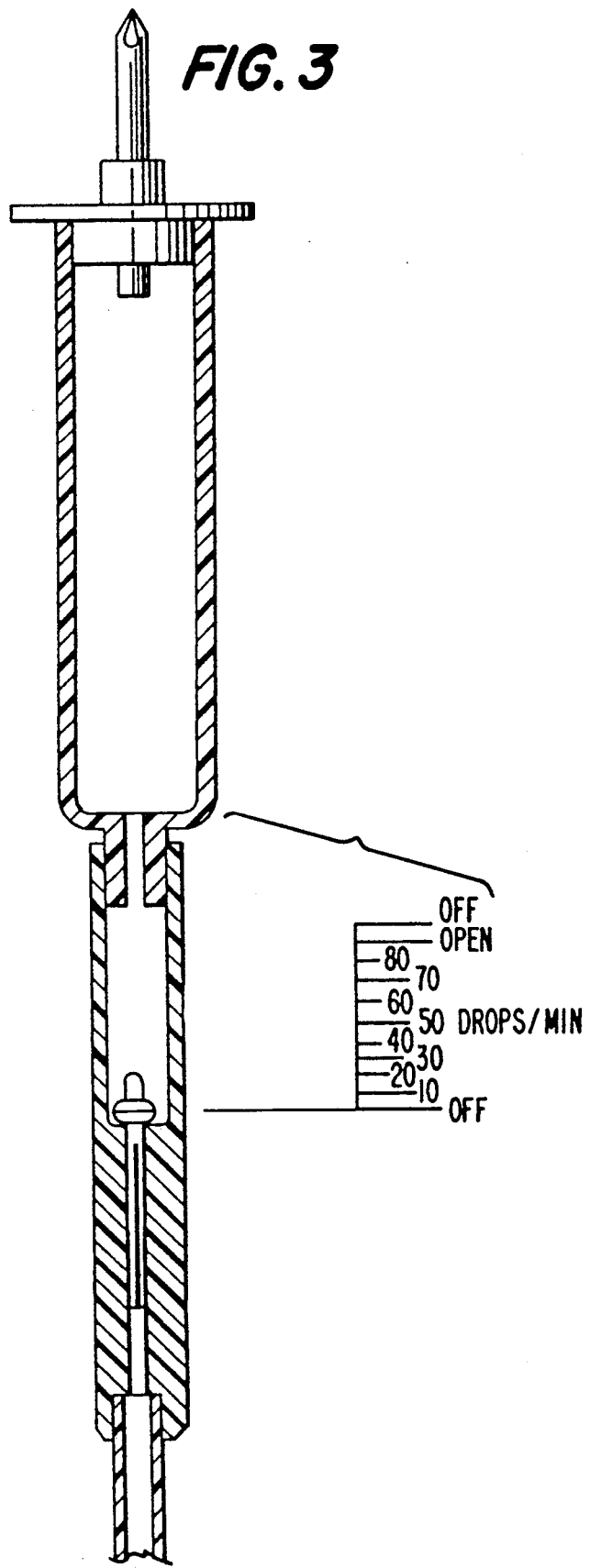

FLOW REGULATOR AND METHOD

TECHNICAL FIELD

The present invention relates to a flow regulator and method for controlling fluid flow rate. More particularly, the invention relates to a flow regulator and method for regulating the flow rate of liquid to be administered parenterally to a patient.

BACKGROUND ART

The administration of liquids parenterally to a patient is a treatment that has been employed for many years. It typically involves the use of a container of liquid to be infused, an elongated flexible tube for conveying the liquid from the container to a patient and a cannula or catheter for insertion into the cardiovascular system of the patient to introduce the liquid for infusion into the patient. A variety of liquids may be infused in this manner, including dextrose, saline, Ringers solution, and water or any combination of these solutions. Others include whole blood plasma. More recently, drugs such as antibiotics, heprine, etc. are administered in this manner.

The most common manner of controlling the flow of the liquid being administered parenterally to the patient has been to selectively collapse a portion of the flexible delivery tube using a roller clamp, for example. The rate of flow in such cases is determined by the rate at which drops of liquid are observed falling through a drip chamber.

Gravity infusion of the parenteral solution is accomplished by suspending the solution container several feet above the patient and connecting the solution container to the venepuncture site via a disposable intravenous administration set which includes the drip chamber and flexible delivery tube U.S. Pat. No. 4,175,558 discloses an example of a roller clamp for collapsing the delivery tube to control the flow rate.

The roller clamp is a simple, two-piece plastic device that progressively compresses the plastic tube of the intravenous administration set at a single point on the tube thereby occluding the tube to create a pressure drop across the restriction and a corresponding reduction in flow rate. However, the use of such roller clamps is problematical due to cold flow or creep of the plastic tubing at the point of restriction, which causes the flow rate to decrease after setting. This circumstance requires repeated checking and resetting by the user.

Additionally, because the plastic tube is restricted at a single point by the roller clamp, high resolution of the flow rate of the fluid through the pinched orifice is difficult to achieve. That is, a very slight change in orifice size creates a large change in the flow rate.

Several flow rate regulators such as the Abbott Laboratories' Dial-A-Flow, see, U.S. Pat. No. 3,877,428, have been introduced in recent years in attempts to overcome the aforementioned disadvantages associated with the use of conventional roller clamps. While these known devices do provide more accurate control of the flow rate than the conventional roller clamp, they are multi-component devices which cost more than the actual intravenous administration set to produce.

Moreover, these known flow rate regulators usually incorporate an elastomeric seal. In high volume production, a small percentage of the flow rate regulators can experience leaks about their elastomeric seals. This prevents the positioning of these devices in an elevated position close to the intravenous administration set drip chamber since in that location a leak would admit air to the system and introduce the danger of emboli to the patient. Therefore, with these known flow regulators, the drip chamber and flow regulator are normally located in spaced relation. This makes it inconvenient for the user when setting the flow rate and monitoring the drip rate since these are accomplished at different locations.

The aforementioned known flow regulators of the type disclosed in U.S. Pat. No. 3,877,428 are based on the Poiseuille equation for uniform laminar, non-turbulent flow. That is, the flow rate control is achieved by changing the length of a fluid path of small cross-section. This manner of operation provides much better accuracy and resolution than the "orifice" type of operation employed in the conventional roller clamp application. The components of the flow regulators providing the small cross-section fluid path can be mass produced by plastic injection molding in a repeatable manner which results in consistent flow performance of these devices.

DISCLOSURE OF INVENTION

An object of the present invention is to provide an improved flow regulator and method for controlling the flow rate of a fluid, particularly a liquid to be administered parenterally to patient, which flow regulator and method, are simple and inexpensive, but provide superior accuracy and performance in flow rate control as compared with the conventional roller clamp.

A further object of the invention is to provide an improved flow regulator and method which permit the flow regulator to be conveniently located immediately adjacent the drip chamber of the intravenous administration set without fear of the ingress of air due to leakage about an elastomeric seal, the flow regulator of the present invention eliminating the need for such an elastomeric seal.

An additional object of the invention is to provide an improved flow regulator wherein the flow rate is controlled by the provision of a small cross-section flow channel having a length which can be varied for accurately adjusting and maintaining the flow rate but which regulator has only a small number of simple, low cost parts as compared with known flow regulators which achieve such rate control.

These and other objects of the invention are attained by the improved flow regulator of the invention for controlling the flow rate of liquid to be administered parenterally to a patient, the flow regulator comprising a first member having a flow passage therein for a liquid to be administered parenterally to a patient. A second member is arranged to be adjustably telescoped in the passage of the first member. The first and second members are constructed such that the second member can be arranged in the passage of the first member to partially obstruct the flow passage to form a flow rate controlling channel which restricts the flow rate as a function of the length of the channel. The length of the flow rate controlling channel is adjustable by changing the relative position of the first and second members. Means are also provided for changing the relative position of the first and second members to permit adjustment of the length of the flow rate controlling channel and thereby the flow rate of liquid flowing through the flow regulator.

The disclosed, preferred embodiment of the flow regulator further comprises a drip chamber for receiving liquid from a supply of liquid to be administered parenterally to a patient. The drip chamber permits detection of drops of liquid passing through the drip chamber and is located upstream of the second member of the flow regulator along a liquid flow path for delivering liquid from a supply of liquid to a patient by way of the flow regulator. The flow regulator with drip chamber can also form part of an intravenous solution administration set wherein the drip chamber includes a spike connector for connection to a liquid supply and a plastic tube to convey the solution from the flow regulator to the venepuncture site.

An additional feature of the flow regulator is that the flow passage thereof includes a rate control chamber located upstream of the flow rate controlling channel. A portion of the second member is located in the rate control chamber. The disclosed, preferred embodiment of the flow regulator employs a first member having a wall about the rate controlling chamber which is flexible to allow application of a generally radially directed adjusting pressure to the second member portion within the rate controlling chamber through the application of an external force on the wall of the flow regulator.

A generally radially directed adjusting force applied to the exterior wall of the flow regulator as by the application of pressure from the thumb and forefinger to the respective, opposite sides of the first member results in axial translation of the second member along the flow passage in the first member for changing the length of the flow rate controlling channel and thereby the flow rate. More specifically, an enlargement on the portion of the second member located within the rate controlling chamber includes force reacting surfaces which each form an acute angle with a longitudinal axis of the flow passage of the first member for reacting the generally radial pinching forces on the flexible wall of the first member which is transmitted to the reacting surface to produce axially directed forces to affect the axial translation of the second member within the flow passage of the first member. The volume of the rate controlling chamber is preferably less than one-half that of the drip chamber to avoid flooding the drip chamber during rate adjustment.

The relative position of the first and second members can be changed between a first position where the length of the flow rate controlling channel is relatively short for producing a relatively fast flow rate, and a second position where the length of the flow rate controlling channel is relatively long for producing a relatively slow flow rate. The relative position of the first and second members and hence the length of the flow rate controlling channel can be continuously varied between the first and second positions for continuously changing the flow rate of liquid through the regulator.

In a third position the second member completely obstructs the flow passage to prevent liquid flow through the regulator. This third position is located adjacent the second position. The relative position of the members can also be set at a fourth, open position adjacent the first position for allowing the flow of liquid through the passage and regulator without substantially restricting the flow rate of the liquid. In this position the liquid is bypassed around the flow rate controlling channel through a full flow channel.

A fifth position, which is adjacent the fourth, open position, also results in obstruction of the flow passage to prevent liquid flow through the regulator. The use of two off positions is preferred since it provides the user with an off position adjacent to the open position when priming and setting up the infusion and, equally important, is the ability to stop the infusion from a low flow rate setting without moving through the full open position.

According to the disclosed form of the invention, the outer surface of the second member has a first channel formed therein which extends along a portion of the length of the second member. The channel and a surface of the first member which defines a smaller diameter portion of the flow passage, cooperate to form the flow rate controlling channel when positioned opposite one another. As noted above, the means for allowing a substantially unrestricted flow of liquid through the regulator comprises a second, full flow channel. This channel is also formed in the outer surface of the second member in spaced relation to the first channel for cooperation with an opposing surface of the first member defining the flow passage.

As a further feature of the invention, at least a portion of the second member is adjustably telescoped in the flow passage of the first member with an interference fit. This advantageously retains the second member in its set position within the passage of the first member to maintain the set length of the flow rate controlling channel and thereby the flow rate of liquid through the regulator until otherwise adjusted by the user. To facilitate such an adjustment or movement of the second member, at least one of the surface of the first member defining the flow passage and the portion of the surface of the second member interference fit therewith, has a friction reducing coating thereon. Preferably, the friction reducing coating is a water insoluble hydrogel coating.

Advantageously, the flow rate controlling second member of the flow regulator is totally contained within the passage of the first member for adjusting the flow rate of liquid flowing through the regulator whereby an elastomeric seal is unnecessary and the likelihood of leakage of air into the system can be avoided. Illustratively, the first member can be in the form of a seamless, flexible tubular shaped member for preventing leakage of air leakage into the liquid being administered to the patient. This enables the flow regulator to be located immediately downstream of the drip chamber for convenience in observation and setting the flow rate by the user. Also, since only a single flow rate controlling member located wholly within the means defining the flow passage is used, a simple, inexpensive flow regulator is possible which, at the same time, enables the accurate setting and maintenance of liquid flow rates.

The method of controlling the flow rate of a liquid to be administered parenterally to a patient according to the invention comprises the steps of providing a flow rate controlling member within a flow passage of a flow regulator such that the flow rate controlling member can be adjustably positioned within the passage for adjusting the flow rate of liquid flowing through the regulator, and adjusting the position of the flow rate controlling member within the flow passage by the application of an adjusting force to the outside of the flow regulator. The flexible wall of the flow regulator transmits the generally radially directed adjusting force to the flow rate controlling member through a load reacting surface provided along an enlarged portion of the flow rate controlling member to produce an axially directed force component for moving the second member.

These and other objects, feature and advantages of the present invention will become more apparent from the following description when taken in connection with the accompanying drawings which show, for purposes of illustration only, one embodiment in accordance with the invention.

BRIEF DESCRIPTION OF DRAWINGS

FIG. 1 is a side view, partially in cross-section, along the longitudinal center axis of a flow regulator according to a preferred embodiment of the invention;

FIG. 1A is an illustration of the flow rate control indicia which appear on the side of the flow regulator shown in FIG. 1;

FIG. 2 is an enlarged cross-sectional view of the flow rate controlling member taken along the line II—II in FIG. 1 and illustrating the small cross-sectional area, triangular shaped channel in the outer surface of the member;

FIG. 3 is a side view of the flow regulator like FIG. 1 except that the flow rate controlling member is set in a first off position adjacent the lower flow rate setting;

BEST MODE FOR CARRYING OUT THE INVENTION

Figure 4:
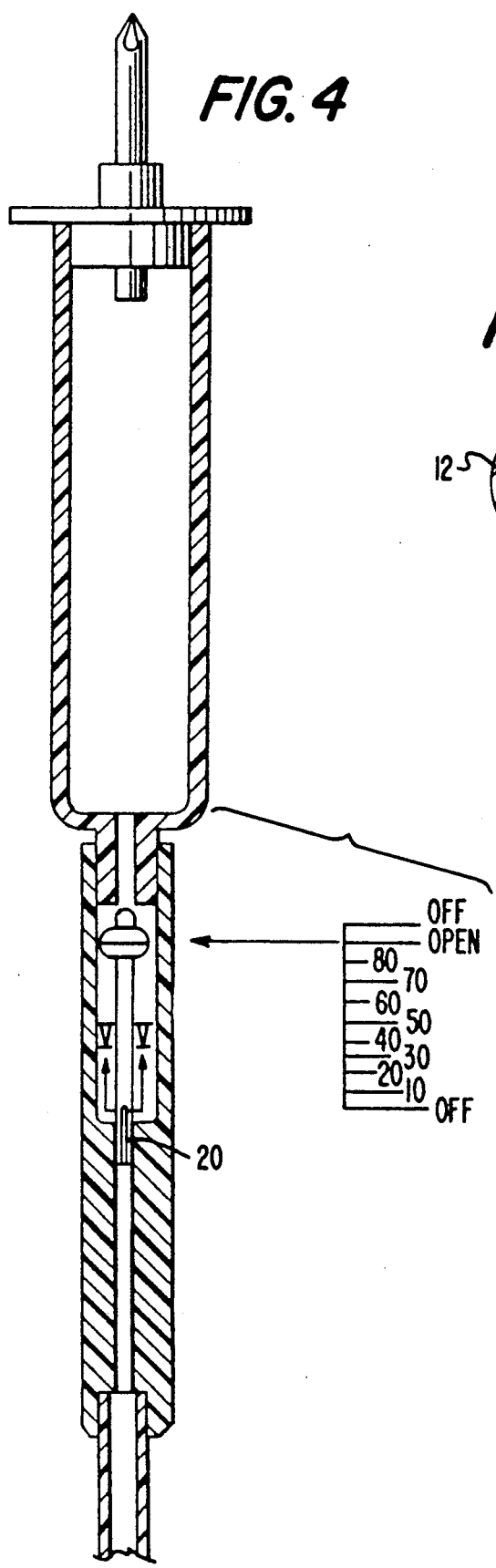
FIG. 4 is a cross-sectional view of the flow regulator of FIG. 1 but taken from the opposite side and depicting a full flow channel in use in the open position of the flow rate controlling member.

Referring now to the drawings, a flow regulator 1 according to the invention is shown as an integral part of an intravenous administration set 2. The IV set 2 comprises, in addition to the flow regulator 1, a drip chamber 3 and plastic tubing 4. The administration set 2 is adapted to be connected to a container of liquid, not shown, by way of a conventional spike connector 5 at the upper end of the drip chamber 3 for conveying liquid to a venepuncture site of a patient by way of the drip chamber 3, flow regulator 1 and plastic tubing 4. The liquid container is elevated above the patient in a conventional manner for gravity infusion of the parenteral solution by way of the administration set.

The outlet 6 at the lower end of the drip chamber 3 is connected to a first member 7 of flow regulator 1. The outlet and first member are both formed of plastic and the connection between them can be formed by solvent bonding, for example. The first member 7 has a flow passage 8 therein between an inlet and an outlet of member 7. The flow passage 8 includes a relatively large diameter rate control chamber 9 and a relatively smaller diameter portion 10 located directly beneath the rate control chamber 9. A passage 11 through the outlet 6 of the drip chamber also forms a portion of the flow passage at the inlet there of which is used to control the flow of liquid to be administered parenterally to the patient. The lower end of the first member 7 is solvent bonded to plastic tubing 4 for conveying liquid to the venepuncture site.

The flow regulator 1 further includes a second, flow rate controlling member 12 which is arranged to be adjustably telescoped in the flow passage 8 of the flow regulator 1. The flow rate controlling member 12 is generally in the form of an elongated, straight pin which has a bulbous enlargement 13 securely connected or integrally formed therewith near the upper end of the member. Apart from the configuration of the enlargement 13, the member 13 is uniformly cylindrical with a diameter which, in the illustrated embodiment, is 0.1 inch. The overall length of the member 12 is approximately one and five-eights inches.

The relatively small diameter portion 10 of the flow passage 8 and also the passage 11 through the outlet 6 are cylindrical passages with a diameter which is slightly less than the outside diameter of the second member 12 for forming an interference fit with the second member. Preferably, the diameter of the passages 8 and 11 is between 1% and 6% less than the outside diameter of the second member 12. To avoid a substantial amount of friction with relative movement of the second member 12 interference fit in the passages 8 and 11, the flow rate controlling member and/or the inside of the passages 8 and 11 are coated with a water insoluble hydrogel, particularly a hydrophilic graft polymer or copolymer such as glycol acrylate, glycol methacrylate, methacrylamide, acrylmide or the like generally described in U.S. Pat. Nos. 2,976,576 and 3,220,960, for example. The coating is preferably applied as a thin liquid film and then polymerized in situ by ultraviolet radiation. The resulting surfaces are non-toxic, biocompatible and have an extremely low coefficient of friction under aqueous conditions which reduces the axial force required to move the flow rate controlling member to a very low value for ease in affecting a rate change. However, sufficient resistance to movement of the member 12 remains in order that a flow rate setting remains the same until otherwise adjusted by the user.

The rate controlling member 12 is preferably an injection molded component made from a thermoplastic material such as polystyrene. The member 12 is formed with a small cross-sectional area channel 14 in the outer surface of the member extending from the lower end thereof upwardly a distance of about one inch. The channel 14 has a triangular cross-section as shown in FIG. 2. When telescoped in the relatively small diameter portion 10 of the fluid passage of the flow regulator, the channel 14 and the surface of the first member 7 defining the passage 10 form a flow rate controlling channel 15 of variable length L which restricts the flow rate as a function of the length of the channel 15. In the illustrated embodiment, the flow rate controlling channel 15 has a cross-sectional area 0.0001 square inch. The length L of the flow rate controlling channel 15 is adjusted by moving the second member 12 along the axis of the flow passage 8. The restricted fluid path length L is designed to correspond to the drop rate setting scale 16 which is printed on the outside of the first member 7. The first member 7 is also an injection molded component made from a transparent, flexible thermoplastic such as polyvinyl chloride. In order to provide adequate support against hoop stress induced in the first member by the interference fit of the second member in the passage 10, the wall thickness of the first member in the vicinity of the passage 10 is preferably at least 80% of the diameter of the cylindrical body of second member 12.

The volume of the rate control chamber 9 in first member 7 is preferably less than or equal to one-half the volume of the associated drip chamber 3 located upstream of the rate control chamber. As a result, flooding of the drip chamber during adjustment of the flow rate can be avoided. If the drip chamber is flooded, it is not possible to count drops for detecting the flow rate.

The channel 14 ends a short distance below the underside of the enlargement 11 on the second member 12 to provide a sealed, off position when the unchanneled area 17 on the surface of the member 12 is telescoped within the passage portion 10 as shown in FIG. 3. A line 18 can be formed on the outer surface of the enlargement 14 for easily visually determining the setting of the flow rate controlling member 12 relative to the adjacent drop rate setting scale 16. Alternatively, at least the enlargement 13 could be formed of a dark colored plastic for visual contrast against the adjacent scale 16.

Figure 6:
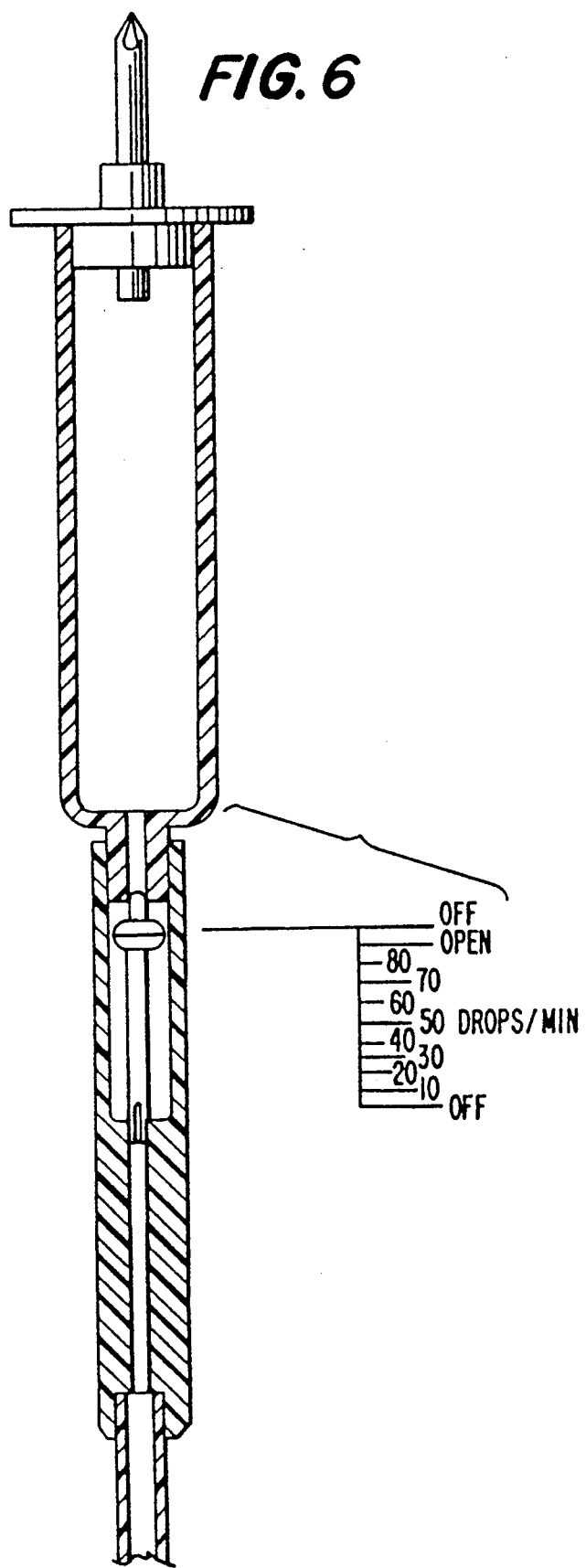
FIG. 6 is a side view of the flow regulator like FIG. 4 except that the flow rate controlling member is shown positioned in a second off position which is adjacent the open position.

The short extension 19 of the flow rate controlling member 12 located above the enlargement 13 provides a second off position at the other end of the permitted path of axial translation of the second member 12. The extension 19 is received with an interference fit in the passage 11 for obstructing flow through the flow passage 8 of the flow regulator. The flow rate controlling member 12 can be seen in this second off position in FIG. 6.

An open position for full, substantially unrestricted flow of liquid through the flow regulator is located between the higher flow rate setting on the continuous scale of flow rates and the second off position. Unrestricted flow through the device is achieved by the provision of a full flow channel 20 formed in the outer surface at the lower end of second member 12. The full flow channel 20 is evident in FIGS. 4–6 of the drawings wherein it can be seen that the cross-sectional area of the full flow channel is substantially greater than the small cross-sectional area channel 14 so as not to restrict the flow rate of liquid. The channel 20 extends over only a short distance at the lower end of the second member 12 as seen in FIG. 4 for opening the flow regulator when the second member is positioned in the open position. The open position is useful for priming and setting up the infusion, for example.

Figure 5:
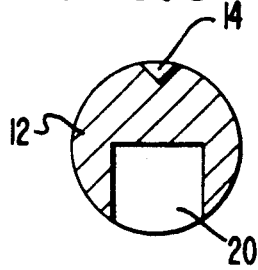
FIG. 5 is an enlarged cross-sectional view of the flow rate controlling member taken along the line V—V in FIG. 4.

The provision of two off positions at respective ends of the travel of the flow rate controlling member 12 is particularly useful in enabling the user to quickly move from the off position to an open position when priming and setting up infusion. Equally important is the ability to stop the infusion from a lower flow rate setting without moving through the full open position. The full flow channel 20 and the small cross-sectional area channel 14 are located on opposite sides of the second member 12 as seen in FIG. 5. Both of the channels can be molded into the second member 12. However, these channels could be molded into the first member as an alternative method of construction.

Figure 7:
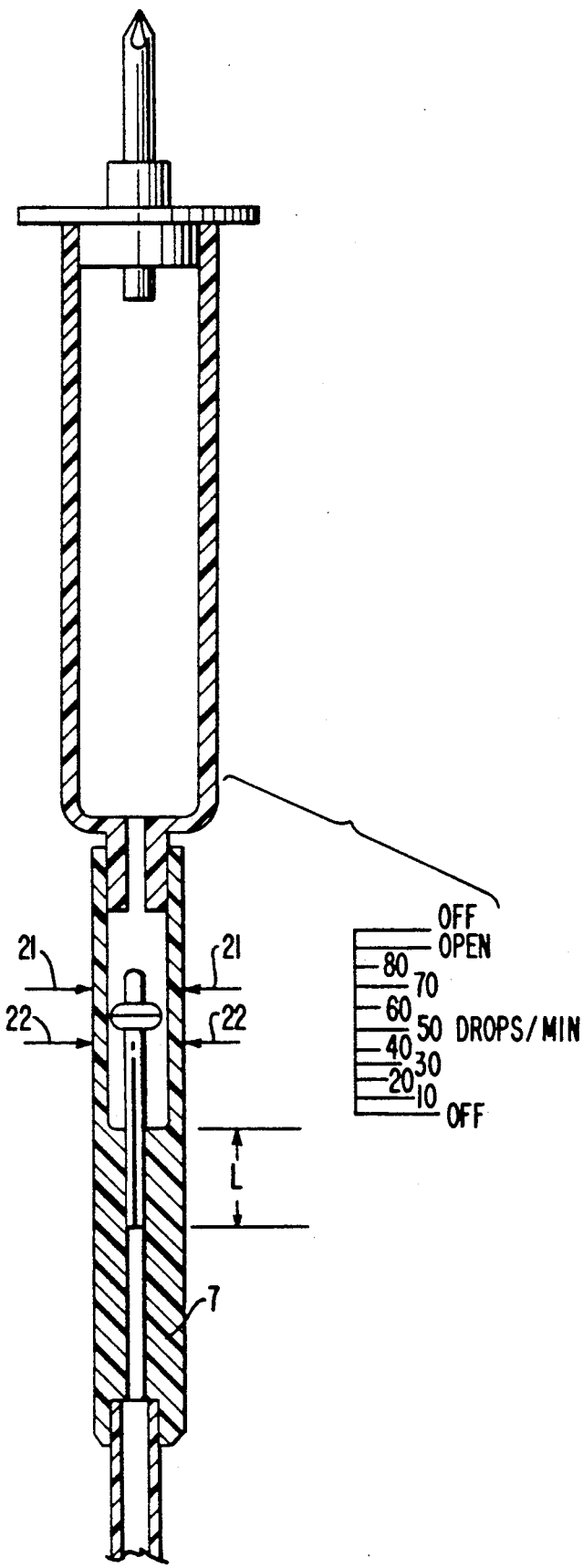
FIG. 7 is a side view of the flow regulator like FIG. 1 and illustrating the flexible nature of the outer wall for pressing the flow rate controlling member to adjust the flow rate.

In operation, the axial position of the flow rate controlling member 12 in the flow passage 8 of the first member 7 is adjusted by pressing inwardly on the relatively thin, flexible wall of the first member 7 about the rate control chamber 9 either immediately above or below the enlargement 13 of the flow rate controlling member. Preferably, this pressing is accomplished using the thumb and forefinger which are applied on opposite sides of the first member 7. When the centripetal or radially inwardly directed force is applied in the locations of arrows 21 in FIG. 7, that is, slightly above the enlargement 13, the outer load reacting surface of the enlargement, arranged at an acute angle with respect to the longitudinal axis of the flow regulator, is contacted by the fixed inner surface of the flexed wall of the first member defining the rate control chamber 9, see the dashed line contour in FIG. 7. An axially directed force component results which moves the flow rate controlling member downward for increasing the length L of the flow rate controlling channel 15 thereby reducing the flow rate as can be seen from the indica on scale 16. Similarly, inwardly directed forces at the location of arrows 22 would result in upward movement of the second member within the flow passage 8 of the flow regulator for decreasing the flow rate.

The drop/minute scale illustrated in the disclosed embodiment will of course change depending upon the number of drops per milliliter the drip chamber is designed for. Usual standards in the industry are 10, 15, 20 and 60 drops per milliliter. The flow regulator should be calibrated to accommodate a dynamic range between 20 and 250 milliliters/hour converted to drops per minute.

From the above it can be seen that the improved flow regulator and method of the invention associated with the use of the flow regulator permit accurate adjustment and maintenance of the flow rate using only a small number of simple, low cost parts are compared with known flow regulators. Moreover, the flow regulator of the invention does not employ an elastomeric seal whereby leakage can be avoided and the flow regulator can be conveniently located immediately below a drip chamber. The simplicity and low cost of the flow regulator also compare favorably with the conventional roller clamp thereby eliminating the need for an expensive flow regulator.

While I have shown and described only one embodiment in accordance with the present invention, it is understood that the same is not limited thereto, but is susceptible to numerous changes and modifications as known to those skilled in the art. For example, it is envisioned that the flow regulator of the invention is applicable for regulating the flow of fluids other than those to be administered parenterally to a patient. For example, the flow regulator would be useful for controlling the flow of paints, dyes, cosmetics and the like for continuous mixing and proportioning. Further, the flow regulator would be useful in metering low percentage additions in chemical processes. Therefore, I do not wish to be limited to the details shown and described herein, but intend to cover all such changes and modifications as are encompassed by the scope of the appended claims.

I claim:

1. A flow regulator for regulating the flow of liquids to be administered parenterally to a patient comprising a first member having a flow passage therein with an inlet and an outlet for a liquid to be administered parenterally to a patient, a second member arranged to be adjustably telescoped in the passage of the first member, said first and second members being constructed such that the second member can be arranged in the passage of the first member to partially obstruct the flow passage to form a flow rate controlling channel which restricts the flow rate as a function of the length of said channel, the length of the flow rate controlling channel being adjustable, by changing the relative position of the first and second members, and means for changing the relative position of the first and second members to adjust the length of the flow rate controlling channel and thereby the flow rate of liquid flowing through said flow regulator, wherein said means for changing comprises a flexible wall of said first member which defines at least a portion of the flow passage and which transmits pressure applied to the outside of the first member to the second member for adjusting its position in the passage to adjust the flow rate of liquid flowing through the regulator.

2. A flow regulator according to claim 1, in combination with a drip chamber for receiving liquid from a supply of liquid to be administered parenterally to a patient, said drip chamber permitting detection of drops of liquid passing through the drip chamber, and means connecting the drip chamber to the first member of the flow regulator such that the drip chamber is located upstream of the second member along a liquid flow path for delivering liquid from a supply of liquid to a patient by way of said flow regulator.

3. A flow regulator according to claim 2, wherein said flow passage includes a rate control chamber in said first member of said flow rate controlling channel, a portion of said second member being located in said rate control chamber.

4. A flow regulator according to claim 3, wherein said flexible wall includes a wall of said first member defining said rate controlling chamber which is flexible to allow application of adjusting pressure to said portion of the second member located in the rate controlling chamber through the application of an external force on said flexible wall of said first member.

5. A flow regulator according to claim 3, wherein the volume of the rate control chamber is less than one-half that of the drip chamber.

6. A flow regulator according to claim 1, wherein the relative position of the first and second members can be changed between a first position where the length of the flow rate controlling channel is relatively short for a flow rate which is relatively fast and a second position where the length of the flow rate controlling channel is relatively long for a flow rate which is relatively slow.

7. A flow regulator according to claim 6, wherein the relative position of said first and second members can be varied continuously between said first and second positions to continuously vary the length of the flow rate controlling channel for changing the flow rate of liquid through the regulator.

8. A flow regulator according to claim 6, wherein said second member completely obstructs the flow passage to prevent liquid flow through the regulator when said first and second members are positioned relative to one another in a third position which is located adjacent said second position.

9. A flow regulator according to claim 6, wherein the relative position of the first and second members can be changed to a fourth, open position adjacent said first position wherein means are provided for allowing the flow of liquid through said passage without substantially restricting the flow rate of the liquid.

10. A flow regulator according to claim 9, wherein said means for allowing the substantially unrestricted flow of liquid comprises a full flow channel formed in said second member.

11. A flow regulator according to claim 9, wherein the relative position of the first and second members can be changed to a fifth position, which is adjacent said fourth, open position, wherein the second member completely obstructs the flow passage to prevent liquid flow through the regulator.

12. A flow regulator according to claim 1, wherein the outer surface of the second member has a channel formed therein which extends along a portion of the length of said second member, the channel in the outer surface of the second member and a surface of the first member defining said flow passage cooperating to form said flow rate controlling channel.

13. A flow regulator according to claim 1, wherein at least a portion of said second member is adjustably telescoped in the flow passage of said first member with an interference fit.

14. A flow regulator according to claim 13, wherein at least one of the surface of the first member defining the flow passage and the outer surface of the portion of said second member which is interference fit therein has a friction reducing, water insoluble hydrogel coating thereon.

15. A flow regulator according to claim 1, wherein said flow passage includes a rate control chamber in said first member upstream of said flow rate controlling channel, a portion of said second member being located in said chamber.

16. A flow regulator according to claim 15, wherein said flexible wall includes a wall of said first member defining said rate control chamber which is flexible to allow application of the adjusting pressure to said portion of the second member in the rate control chamber through the application of an external force to the wall defining the rate control chamber.

17. A flow regulator according to claim 1, wherein said means for changing permits movement of said second member axially along the flow passage in said first member between two spaced end positions, and wherein means are provided for completely obstructing the flow passage to prevent liquid flow through the flow regulator when the second member is positioned at each of said end positions.

18. A flow regulator according to claim 1, wherein said second member is contained entirely within the passage of said first member, at least a portion of said first member being transparent so that the relative position of the second member within the first member can be readily visually observed.

19. A flow regulator according to claim 1, wherein said flow passage extends along an axis, said second member is movable along the axis of the flow passage for adjusting the relative position of the first and second members and the flow rate, said second member including an enlarged portion having an adjusting force reacting surface which is arranged at an acute angle with respect to the axis of said flow passage, said force reacting surface reacting generally radially directed force applied to said reacting surface through said flexible wall for moving said second member in the axial direction of said flow passage.

20. A flow regulator for regulating the flow of liquid to be administered parenterally to a patient comprising means defining a passage through said flow regulator from an inlet to an outlet along which liquid to be administered parenterally to a patient can be flowed, a flow rate controlling member totally contained and adjustably positioned within said passage for adjusting the flow rate of liquid flowing through the regulator, and means for transmitting pressure applied to the outside of the flows regulator to said rate controlling member for adjusting its position in the passage to adjust the flow rate of liquid flowing through the regulator, and wherein said means for transmitting pressure comprises a flexible wall of said means defining a passage.

21. A method of regulating the flow of liquid to be administered, in vitro, parenterally to a patient comprising providing a flow rate controlling member inside of flow passage of a flow regulator through which liquid to be administered parenterally to a patient can be flowed between an inlet and an outlet of the flow regulator, at least a portion of the flow passage being defined by a flexible wall of the flow regulator, and adjusting the position of the flow rate controlling member within the flow passage for adjusting the flow rate of liquid flowing through the regulator by applying a force to the outside of the flexible wall of the flow regulator which is flexed to transmit a force to the flow rae controlling member within the flow regulator for adjusting the position of the flow rate controlling member in the flow passage to adjust the flow rate of liquid flowing through the regulator.

22. A method according to claim 21, further comprising the step of moving the flow rate controlling member to a position within the passage of the flow regulator to completely obstruct the passage for preventing the flow of liquid through the flow regulator.

23. A flow regulator for fluids comprising a regulator body having an inlet and an outlet and a fluid flow passage therein extending between the inlet and the outlet, a flow rate controlling member arranged wholely within the flow passage of the regulator body to be adjustably telescoped in the passage, said regulator body and flow rate controlling member being constructed such that the member can be arranged in the flow passage of the body to partially obstruct the flow passage to form a flow rate controlling channel which restricts the flow rate as a function of the length of said channel, the length of the flow rate controlling channel being adjustable, by changing the relative position of the body and the member, and means for changing the relative position of the body and the member to adjust the length of the flow rate controlling channel and thereby the flow rate of fluid flowing through said flow regulator.

24. An intravenous solution administration set including a flow regulator for liquids to be administered parenterally to a patient comprising a first member having a flow passage therein with an inlet and an outlet for a liquid to be administered parenterally to a patient, a second member arranged to be adjustably telescoped in the passage, said first and second members being constructed such that the second member can be arranged in the passage of the first member to partially obstruct the flow passage to form a flow rate controlling channel which restricts the flow rate as a function of the length of said channel, the length of the flow rate controlling channel being adjustable for adjusting the flow rate, by changing the relative position of the first and second members to adjust the length of the flow rate controlling channel and thereby the flow rate of liquid flowing through said flow regulator, wherein said first member includes a flexible wall which defines at least a portion of the flow passage whereby the position of the second member in the passage can be adjusted through the application of an adjusting force to the second member through said flexible wall from outside of said first member; a drip chamber for receiving liquid from a supply of liquid to be administered, in vitro, parenterally to a patient, said drip chamber permitting detection of drops of liquid passing through the drip chamber, means connecting the drip chamber to the inlet of the flow passage of the regulator such that the drip chamber is located upstream of the second member along a liquid flow path for delivering liquid from a supply of liquid to a patient by way of said flow regulator; and a tubing for conveying liquid from the flow regulator to a patient and means connecting the tubing to the outlet of the flow passage of the first member.

* * * * *